United States Patent
Barnes et al.

(10) Patent No.: US 12,351,610 B2
(45) Date of Patent: Jul. 8, 2025

(54) INTERFERON REGULATORY FACTOR 5 INHIBITORS AND USES THEREOF

(71) Applicant: THE FEINSTEIN INSTITUTES FOR MEDICAL RESEARCH, Manhasset, NY (US)

(72) Inventors: Betsy J. Barnes, Glenwood Landing, NY (US); Shan Sun, Wingdale, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 805 days.

(21) Appl. No.: 17/608,487

(22) PCT Filed: May 4, 2020

(86) PCT No.: PCT/US2020/031283
§ 371 (c)(1),
(2) Date: Nov. 3, 2021

(87) PCT Pub. No.: WO2020/227194
PCT Pub. Date: Nov. 12, 2020

(65) Prior Publication Data
US 2022/0220168 A1  Jul. 14, 2022

Related U.S. Application Data

(60) Provisional application No. 62/844,894, filed on May 8, 2019.

(51) Int. Cl.
*C07K 14/47* (2006.01)
*A61K 38/00* (2006.01)
*A61P 37/00* (2006.01)

(52) U.S. Cl.
CPC .............. *C07K 14/47* (2013.01); *A61P 37/00* (2018.01); *A61K 38/00* (2013.01)

(58) Field of Classification Search
CPC .......................... C07K 14/47; C07K 14/4702; C07K 2319/10; A61P 37/00; A61P 37/02; A61K 38/00
See application file for complete search history.

(56) References Cited

U.S. PATENT DOCUMENTS

| | | |
|---|---|---|
| 2014/0030218 A1* | 1/2014 | Udalova ............ C07K 14/4702 514/1.9 |
| 2014/0273091 A1 | 9/2014 | Acton et al. |
| 2016/0009772 A1 | 1/2016 | DeMartino et al. |
| 2016/0152678 A1 | 6/2016 | Bancel et al. |
| 2018/0258148 A1 | 9/2018 | Barnes |
| 2021/0254056 A1 | 8/2021 | Abdulov |
| 2021/0403520 A1 | 12/2021 | Barnes |

FOREIGN PATENT DOCUMENTS

| | | | |
|---|---|---|---|
| WO | 2013/151672 A2 | 10/2013 | |
| WO | 2013/151672 A3 | 3/2014 | |
| WO | WO-2017044855 A2 * | 3/2017 | ............. A61P 37/02 |
| WO | 2017/044855 A3 | 7/2017 | |
| WO | 2018/204764 A1 | 11/2018 | |

OTHER PUBLICATIONS

European Patent Office, "Extended European Search Report," issued in European Patent Application No. 20 802 411.7, which is a counterpart of U.S. Appl. No. 17/608,487, on May 10, 2023, 14 pages.
Canadian Intellectual Property Office, "First Examiner's Report," issued in Canadian Patent Application No. 3,139,695, which is a counterpart of U.S. Appl. No. 17/608,487, on Apr. 5, 2023, 7 pages.
PCT International Search Report dated Aug. 28, 2020 in connection with PCT/US2020/031283.
PCT Written Opinion of the International Searching Authority Report dated Aug. 28, 2020 in connection with PCT/US2020/031283.
Thompson et al. "Therapeutic Targeting of IRFs: Pathway-Dependence or Structure-Based?," Frontiers In Immunology, Nov. 20, 2018 (Nov. 20, 2018), vol. 9, Art. No. 2622, pp. 1-13.

* cited by examiner

*Primary Examiner* — Randall L Beane
(74) *Attorney, Agent, or Firm* — Amster, Rothstein & Ebenstein LLP

(57) ABSTRACT

Polypeptides comprising a cell penetrating amino acid sequence and an interferon regulatory factor 5 (IRF5) targeting amino acid sequence are disclosed, where the IRF5 targeting amino acid sequence is one or more of RHATRHG (SEQ ID NO:1), KSRDFRL (SEQ ID NO:2) and GPRDMPP (SEQ ID NO:3), as well as methods of using these polypeptides to treat diseases, such as autoimmune and inflammatory diseases.

11 Claims, No Drawings
Specification includes a Sequence Listing.

SEQUENCE LISTING

```
<160> NUMBER OF SEQ ID NOS: 25

<210> SEQ ID NO 1
<211> LENGTH: 7
<212> TYPE: PRT
<213> ORGANISM: Homo sapiens

<400> SEQUENCE: 1

Arg His Ala Thr Arg His Gly
1               5

<210> SEQ ID NO 2
<211> LENGTH: 7
<212> TYPE: PRT
<213> ORGANISM: Homo sapiens

<400> SEQUENCE: 2

Lys Ser Arg Asp Phe Arg Leu
1               5

<210> SEQ ID NO 3
<211> LENGTH: 7
<212> TYPE: PRT
```

```
<213> ORGANISM: Homo sapiens

<400> SEQUENCE: 3

Gly Pro Arg Asp Met Pro Pro
1               5

<210> SEQ ID NO 4
<211> LENGTH: 17
<212> TYPE: PRT
<213> ORGANISM: Drosophila antennapedia

<400> SEQUENCE: 4

Asp Arg Gln Ile Lys Ile Trp Phe Gln Asn Arg Arg Met Lys Trp Lys
1               5                   10                  15

Lys

<210> SEQ ID NO 5
<211> LENGTH: 16
<212> TYPE: PRT
<213> ORGANISM: Homo sapiens

<400> SEQUENCE: 5

Ala Ala Val Ala Leu Leu Pro Ala Val Leu Leu Ala Leu Leu Ala Pro
1               5                   10                  15

<210> SEQ ID NO 6
<211> LENGTH: 13
<212> TYPE: PRT
<213> ORGANISM: HIV Tat

<400> SEQUENCE: 6

Gly Arg Lys Lys Arg Arg Gln Arg Arg Pro Pro Gln
1               5                   10

<210> SEQ ID NO 7
<211> LENGTH: 17
<212> TYPE: PRT
<213> ORGANISM: Homo sapiens

<400> SEQUENCE: 7

Cys Ser Ile Pro Pro Glu Val Lys Phe Asn Lys Pro Phe Val Tyr Leu
1               5                   10                  15

Ile

<210> SEQ ID NO 8
<211> LENGTH: 17
<212> TYPE: PRT
<213> ORGANISM: Drosophila antennapedia

<400> SEQUENCE: 8

Lys Lys Trp Lys Met Arg Arg Asn Gln Phe Trp Val Lys Val Gln Arg
1               5                   10                  15

Gly

<210> SEQ ID NO 9
<211> LENGTH: 18
<212> TYPE: PRT
<213> ORGANISM: Bovine Lactoferricin

<400> SEQUENCE: 9

Lys Leu Leu Lys Leu Leu Leu Lys Leu Trp Leu Lys Leu Leu Lys Leu
1               5                   10                  15
```

Leu Leu

<210> SEQ ID NO 10
<211> LENGTH: 14
<212> TYPE: PRT
<213> ORGANISM: wasp venom

<400> SEQUENCE: 10

Ile Asn Leu Lys Ala Leu Ala Ala Leu Ala Lys Lys Ile Leu
1               5                   10

<210> SEQ ID NO 11
<211> LENGTH: 18
<212> TYPE: PRT
<213> ORGANISM: Drosophila antennapedia

<400> SEQUENCE: 11

Arg Gln Ile Lys Ile Trp Phe Gln Asn Arg Arg Met Lys Trp Lys Lys
1               5                   10                  15

Gly Gly

<210> SEQ ID NO 12
<211> LENGTH: 27
<212> TYPE: PRT
<213> ORGANISM: wasp venom

<400> SEQUENCE: 12

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 13
<211> LENGTH: 15
<212> TYPE: PRT
<213> ORGANISM: Saccharomyces cerevisiae

<400> SEQUENCE: 13

Tyr Leu Lys Phe Ile Pro Leu Lys Arg Ala Ile Trp Leu Ile Lys
1               5                   10                  15

<210> SEQ ID NO 14
<211> LENGTH: 28
<212> TYPE: PRT
<213> ORGANISM: mouse prion

<400> SEQUENCE: 14

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 15
<211> LENGTH: 16
<212> TYPE: PRT
<213> ORGANISM: Drosophila antennapedia

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 7

```
<212> TYPE: PRT
<213> ORGANISM: Hepatitis B virus

<400> SEQUENCE: 16

Leu Cys Leu Arg Pro Val Gly
1               5

<210> SEQ ID NO 17
<211> LENGTH: 24
<212> TYPE: PRT
<213> ORGANISM: Artificial Sequence
<220> FEATURE:
<223> OTHER INFORMATION: cell penetrating and targeting sequence

<400> SEQUENCE: 17

Asp Arg Gln Ile Lys Ile Trp Phe Gln Asn Arg Arg Met Lys Trp Lys
1               5                   10                  15

Lys Arg His Ala Thr Arg His Gly
            20

<210> SEQ ID NO 18
<211> LENGTH: 24
<212> TYPE: PRT
<213> ORGANISM: Artificial Sequence
<220> FEATURE:
<223> OTHER INFORMATION: cell penetrating and targeting sequence

<400> SEQUENCE: 18

Asp Arg Gln Ile Lys Ile Trp Phe Gln Asn Arg Arg Met Lys Trp Lys
1               5                   10                  15

Lys Lys Ser Arg Asp Phe Arg Leu
            20

<210> SEQ ID NO 19
<211> LENGTH: 24
<212> TYPE: PRT
<213> ORGANISM: Artificial Sequence
<220> FEATURE:
<223> OTHER INFORMATION: cell penetrating and targeting sequence

<400> SEQUENCE: 19

Asp Arg Gln Ile Lys Ile Trp Phe Gln Asn Arg Arg Met Lys Trp Lys
1               5                   10                  15

Lys Gly Pro Arg Asp Met Pro Pro
            20

<210> SEQ ID NO 20
<211> LENGTH: 24
<212> TYPE: PRT
<213> ORGANISM: Artificial Sequence
<220> FEATURE:
<223> OTHER INFORMATION: cell penetrating and targeting sequence

<400> SEQUENCE: 20

Asp Arg Gln Ile Lys Ile Trp Phe Gln Asn Arg Arg Met Lys Trp Lys
1               5                   10                  15

Lys Pro Arg Arg Val Arg Leu Lys
            20

<210> SEQ ID NO 21
<211> LENGTH: 24
<212> TYPE: PRT
<213> ORGANISM: Artificial Sequence
<220> FEATURE:
<223> OTHER INFORMATION: cell penetrating and targeting sequence
```

```
<400> SEQUENCE: 21

Asp Arg Gln Ile Lys Ile Trp Phe Gln Asn Arg Arg Met Lys Trp Lys
1               5                   10                  15

Lys Glu Gly Val Asp Glu Ala Asp
            20

<210> SEQ ID NO 22
<211> LENGTH: 24
<212> TYPE: PRT
<213> ORGANISM: Artificial Sequence
<220> FEATURE:
<223> OTHER INFORMATION: cell penetrating and targeting sequence

<400> SEQUENCE: 22

Asp Arg Gln Ile Lys Ile Trp Phe Gln Asn Arg Arg Met Lys Trp Lys
1               5                   10                  15

Lys Pro Arg Glu Lys Lys Leu Ile
            20

<210> SEQ ID NO 23
<211> LENGTH: 5
<212> TYPE: PRT
<213> ORGANISM: Homo sapiens

<400> SEQUENCE: 23

Asp Trp Glu Tyr Ser
1               5

<210> SEQ ID NO 24
<211> LENGTH: 7
<212> TYPE: PRT
<213> ORGANISM: Homo sapiens

<400> SEQUENCE: 24

Pro Arg Arg Val Arg Leu Lys
1               5

<210> SEQ ID NO 25
<211> LENGTH: 7
<212> TYPE: PRT
<213> ORGANISM: Homo sapiens

<400> SEQUENCE: 25

Pro Arg Glu Lys Lys Leu Ile
1               5
```

INTERFERON REGULATORY FACTOR 5 INHIBITORS AND USES THEREOF

CROSS-REFERENCE TO RELATED APPLICATIONS

This application is a U.S. national stage entry under 35 U.S.C. § 371 of PCT International Patent Application No. PCT/US2020/031283, filed on May 4, 2020, which claims the benefit of U.S. Provisional Patent Application No. 62/844,894, filed on May 8, 2019, the contents of each of which are herein incorporated by reference into the subject application.

STATEMENT OF GOVERNMENT SUPPORT

This invention was made with government support under grant numbers AR065959 and OD012042 awarded by the National Institutes of Health and grant number W81XWH-18-1-0674 awarded by the Department of Defense. The government has certain rights in the invention.

BACKGROUND OF THE INVENTION

Throughout this application various publications are referred to in parentheses. Full citations for these references may be found at the end of the specification immediately preceding the claims. The disclosures of these publications are hereby incorporated by reference in their entireties into the subject application to more fully describe the art to which the subject application pertains.

Systemic lupus erythematosus (SLE) is a debilitating systemic autoimmune disease characterized by elevated levels of circulating anti-nuclear autoantibodies (ANA) that are thought to be caused by immune dysregulation. Immune dysregulation may be conferred by genetic susceptibility and/or environmental triggers. In the past 50 years, only one new drug has been approved for the treatment of SLE—the monoclonal antibody Belimumab. Unfortunately, global immunosuppression to control disease activity remains the standard of care treatment. Thus, extensive efforts are underway to develop drugs against targets involved in disease progression. One such new target is interferon regulatory factor 5 (IRF5), a member of the IRF family of transcription factors. IRF5 was originally identified as a regulator of type I interferons (IFNs) and IFN-stimulated genes (ISGs) in response to virus infection (1-3). Subsequent studies revealed important roles for IRF5 in both innate and adaptive immunity, macrophage polarization, cell growth regulation, and apoptosis (4,5). IRF5 was later identified as an autoimmune susceptibility gene. IRF5 polymorphisms associate with autoimmune and inflammatory conditions, including inflammatory bowel disease, primary biliary cirrhosis, rheumatoid arthritis, systemic lupus erythematosus (SLE), and systemic sclerosis (6-11). Most well-studied is the role of IRF5 in SLE pathogenesis and a common characteristic amongst SLE patients is increased expression of inflammatory cytokines and type I IFNs that contribute to sustained and persistent autoimmunity (12-17). IRF5 expression is significantly elevated in peripheral blood mononuclear cells (PBMC) from SLE patients as compared to age-matched healthy donors (18), and IRF5 is found to be constitutively activated, i.e. nuclear-localized, in SLE monocytes (19). These findings, which implicate IRF5 dysfunction in SLE pathogenesis, are supported by data from multiple models of murine lupus showing that mice lacking Irf5 (i.e., having an Irf5$^{-/-}$ genotype) are protected from disease onset and severity (11,20-22). Equally important and relevant to the therapeutic potential of IRF5 is the finding that lupus disease onset is abrogated in Irf5$^{+/-}$ mice indicating that a reduction in IRF5 expression and/or activity by only half is sufficient for therapeutic effect (23-25).

Although the mechanism(s) by which IRF5 contributes to disease pathogenesis remains unclear, much of the data point to its role in regulating the expression of pro-inflammatory cytokines such as IFNα, interleukin (IL) 6, tumor necrosis factor (TNF) α, and IL12 (3,11,26). Dysregulation of many of these cytokines is associated with disease pathogenesis and IRF5 is predominantly expressed in immune cells (monocytes, dendritic cells and B cells) responsible for their production (26). In an unstimulated cell, IRF5 is localized in the cytoplasm as an inactive monomer (27). While in the inactive conformation, the C-terminal autoinhibitory domain (AID) of IRF5 is thought to either mask the N-terminal DNA binding domain (DBD) and/or the C-terminal protein interaction domain (IAD) that is required for homo/heterodimerization (27,28). Upon activation by post-translational modification events downstream of Toll-like receptors (TLRs), DNA damage, or other antigenic signaling cascades, IRF5 undergoes a conformational change that exposes the IAD for dimerization, and nuclear localization signals (NLS) for translocation (1,27-29). While a significant body of in vitro work suggests this conformational shift is dependent on phosphorylation of C-terminal Serine (Ser) residues by activating kinases (30-32), nuclear translocation remains the essential regulatory step mediating IRF5 transcriptional activity (1,27).

Identification of IRF5 as a global risk factor for autoimmune and inflammatory diseases (11,20-22,33-36), coupled with its increased activation in SLE patient blood, make IRF5 an attractive target for therapeutic inhibition. While C-terminal phosphorylation and dimerization represent steps amenable to inhibition, neither has been definitively shown as an absolute requirement for nuclear translocation (32). An alternate approach to inhibit IRF5 stems from the finding that either N- or C-terminal regions of IRFs can act as dominant negative (DN) mutants to block transactivation ability (2,26,37-41). Though the mechanism(s) by which DN mutants inhibit IRFs remain unclear, their activity suggests that IRF peptide mimetics may be an effective approach for blocking function. Previous studies have described inhibitors of IRF5 nuclear localization and methods of using the inhibitors to treat autoimmune diseases such as SLE (59). The present invention addresses the continuing need for new therapeutics to treat diseases such as autoimmune and inflammatory diseases by inhibiting IRF5.

SUMMARY OF THE INVENTION

The present invention is directed to polypeptides comprising a cell penetrating amino acid sequence and an interferon regulatory factor 5 (IRF5) targeting amino acid sequence, where the IRF5 targeting amino acid sequence is one or more of RHATRHG (SEQ ID NO:1), KSRDFRL (SEQ ID NO:2) and GPRDMPP (SEQ ID NO:3), and to methods of using these polypeptides to treat diseases, such as autoimmune diseases and inflammatory diseases.

DETAILED DESCRIPTION OF THE INVENTION

The invention provides a polypeptide comprising a cell penetrating amino acid sequence and an interferon regulatory factor 5 (IRF5) targeting amino acid sequence, where the IRF5 targeting amino acid sequence is one or more of RHATRHG (SEQ ID NO:1), KSRDFRL (SEQ ID NO:2) and GPRDMPP (SEQ ID NO:3).

In one embodiment, the polypeptide consists essentially of the cell penetrating amino acid sequence and the IRF5 targeting amino acid sequence, wherein addition of any element to the polypeptide does not negatively affect the cell penetrating function of the polypeptide and does not negatively affect the IRF5 targeting function of the polypeptide. In one embodiment, the polypeptide consists of the cell penetrating amino acid sequence and the IRF5 targeting amino acid sequence.

In different embodiments, the cell penetrating amino acid sequence comprises a sequence at least 90% identical to DRQIKIWFQNRRMKWKK (SEQ ID NO:4), AAVALLPAVLLALLAP (SEQ ID NO:5), GRKKRRQRRRPPQ (SEQ ID NO:6), CSIPPEVKFNKPFVYLI (SEQ ID NO:7), KKWKMRRNQFWVKVQRG (SEQ ID NO:8), KLLKLLLKLWLKLLKLLL (SEQ ID NO:9), INLKALAALAKKIL (SEQ ID NO:10), RQIKIWFQNRRMKWKKGG (SEQ ID NO:11), GWTLNSAGYLLGKINLKALAALAKKIL (SEQ ID NO:12), YLKFIPLKRAIWLIK (SEQ ID NO:13), MANLGYWLLALFVTMWTDVGLCKKRPKP (SEQ ID NO:14), RQIKIWFQNRRMKWKK (SEQ ID NO:15) or LCLRPVG (SEQ ID NO:16).

In different embodiments, the cell penetrating amino acid sequence comprises DRQIKIWFQNRRMKWKK (SEQ ID NO:4), AAVALLPAVLLALLAP (SEQ ID NO:5), GRKKRRQRRRPPQ (SEQ ID NO:6), CSIPPEVKFNKPFVYLI (SEQ ID NO:7), KKWKMRRNQFWVKVQRG (SEQ ID NO:8), KLLKLLLKLWLKLLKLLL (SEQ ID NO:9), INLKALAALAKKIL (SEQ ID NO:10), RQIKIWFQNRRMKWKKGG (SEQ ID NO:11), GWTLNSAGYLLGKINLKALAALAKKIL (SEQ ID NO:12), YLKFIPLKRAIWLIK (SEQ ID NO:13), MANLGYWLLALFVTMWTDVGLCKKRPKP (SEQ ID NO:14), RQIKIWFQNRRMKWKK (SEQ ID NO:15) or LCLRPVG (SEQ ID NO:16).

In different embodiments, the cell penetrating amino acid sequence consists essentially of a sequence at least 90% identical to DRQIKIWFQNRRMKWKK (SEQ ID NO:4), AAVALLPAVLLALLAP (SEQ ID NO:5), GRKKRRQRRRPPQ (SEQ ID NO:6), CSIPPEVKFNKPFVYLI (SEQ ID NO:7), KKWKMRRNQFWVKVQRG (SEQ ID NO:8), KLLKLLLKLWLKLLKLLL (SEQ ID NO:9), INLKALAALAKKIL (SEQ ID NO:10), RQIKIWFQNRRMKWKKGG (SEQ ID NO:11), GWTLNSAGYLLGKINLKALAALAKKIL (SEQ ID NO:12), YLKFIPLKRAIWLIK (SEQ ID NO:13), MANLGYWLLALFVTMWTDVGLCKKRPKP (SEQ ID NO:14), RQIKIWFQNRRMKWKK (SEQ ID NO:15) or LCLRPVG (SEQ ID NO:16).

In different embodiments, the cell penetrating amino acid sequence consists essentially of DRQIKIWFQNRRMKWKK (SEQ ID NO:4), AAVALLPAVLLALLAP (SEQ ID NO:5), GRKKRRQRRRPPQ (SEQ ID NO:6), CSIPPEVKFNKPFVYLI (SEQ ID NO:7), KKWKMRRNQFWVKVQRG (SEQ ID NO:8), KLLKLLLKLWLKLLKLLL (SEQ ID NO:9), INLKALAALAKKIL (SEQ ID NO:10), RQIKIWFQNRRMKWKKGG (SEQ ID NO:11), GWTLNSAGYLLGKINLKALAALAKKIL (SEQ ID NO:12), YLKFIPLKRAIWLIK (SEQ ID NO:13), MANLGYWLLALFVTMWTDVGLCKKRPKP (SEQ ID NO:14), RQIKIWFQNRRMKWKK (SEQ ID NO:15) or LCLRPVG (SEQ ID NO:16).

In different embodiments, the cell penetrating amino acid sequence consists of a sequence at least 90% identical to DRQIKIWFQNRRMKWKK (SEQ ID NO:4), AAVALLPAVLLALLAP (SEQ ID NO:5), GRKKRRQRRRPPQ (SEQ ID NO:6), CSIPPEVKFNKPFVYLI (SEQ ID NO:7), KKWKMRRNQFWVKVQRG (SEQ ID NO:8), KLLKLLLKLWLKLLKLLL (SEQ ID NO:9), INLKALAALAKKIL (SEQ ID NO:10), RQIKIWFQNRRMKWKKGG (SEQ ID NO:11), GWTLNSAGYLLGKINLKALAALAKKIL (SEQ ID NO:12), YLKFIPLKRAIWLIK (SEQ ID NO:13), MANLGYWLLALFVTMWTDVGLCKKRPKP (SEQ ID NO:14), RQIKIWFQNRRMKWKK (SEQ ID NO:15) or LCLRPVG (SEQ ID NO:16).

In different embodiments, the cell penetrating amino acid sequence consists of DRQIKIWFQNRRMKWKK (SEQ ID NO:4), AAVALLPAVLLALLAP (SEQ ID NO:5), GRKKRRQRRRPPQ (SEQ ID NO:6), CSIPPEVKFNKPFVYLI (SEQ ID NO:7), KKWKMRRNQFWVKVQRG (SEQ ID NO:8), KLLKLLLKLWLKLLKLLL (SEQ ID NO:9), INLKALAALAKKIL (SEQ ID NO:10), RQIKIWFQNRRMKWKKGG (SEQ ID NO:11), GWTLNSAGYLLGKINLKALAALAKKIL (SEQ ID NO:12), YLKFIPLKRAIWLIK (SEQ ID NO:13), MANLGYWLLALFVTMWTDVGLCKKRPKP (SEQ ID NO:14), RQIKIWFQNRRMKWKK (SEQ ID NO:15) or LCLRPVG (SEQ ID NO:16).

In different embodiments, the polypeptide comprises an amino acid sequence at least 90% identical to DRQIKIWFQNRRMKWKKRHATRHG (SEQ ID NO:17), DRQIKIWFQNRRMKWKKKSRDFRL (SEQ ID NO:18) or DRQIKIWFQNRRMKWKKGPRDMPP (SEQ ID NO:19).

In different embodiments, the polypeptide comprises amino acid sequence DRQIKIWFQNRRMKWKKRHATRHG (SEQ ID NO:17), DRQIKIWFQNRRMKWKKKSRDFRL (SEQ ID NO:18) or DRQIKIWFQNRRMKWKKGPRDMPP (SEQ ID NO:19).

In different embodiments, the polypeptide consists essentially of an amino acid sequence at least 90% identical to DRQIKIWFQNRRMKWKKRHATRHG (SEQ ID NO:17), DRQIKIWFQNRRMKWKKKSRDFRL (SEQ ID NO:18) or DRQIKIWFQNRRMKWKKGPRDMPP (SEQ ID NO:19).

In different embodiments, the polypeptide consists essentially of amino acid sequence DRQIKIWFQNRRMKWKKRHATRHG (SEQ ID NO:17), DRQIKIWFQNRRMKWKKKSRDFRL (SEQ ID NO:18) or DRQIKIWFQNRRMKWKKGPRDMPP (SEQ ID NO:19).

In different embodiments, the polypeptide consists of an amino acid sequence at least 90% identical to DRQIKIWFQNRRMKWKKRHATRHG (SEQ ID NO:17), DRQIKIWF QNRRMKWKKK SRDFRL (SEQ ID NO:18) or DRQIKIWFQNRRMKWKKGPRDMPP (SEQ ID NO:19).

In different embodiments, the polypeptide consists of amino acid sequence DRQIKIWFQNRRMKWKKRHATRHG (SEQ ID NO:17), DRQIKIWFQNRRMKWKKK SRDFRL (SEQ ID NO:18) or DRQIKIWFQNRRMKWKKGPRDMPP (SEQ ID NO:19).

The invention provides an inhibitor of interferon regulatory factor 5 (IRF5) comprising one or more of any of the polypeptides disclosed herein. The invention provides an inhibitor of interferon regulatory factor 5 (IRF5) nuclear translocation comprising one or more of any of the polypeptides disclosed herein. The invention provides polypeptides that bind directly to IRF5 to inhibit IRF5 nuclear translocation.

The invention provides a nucleic acid sequence encoding any of the polypeptides disclosed herein.

The invention provides a pharmaceutical composition comprising one or more of any of the polypeptides disclosed herein and a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution.

The invention provides a method of inhibiting interferon regulatory factor 5 (IRF5) comprising contacting IRF5 with one or more of any of the polypeptides disclosed herein in an amount effective to inhibit IRF5.

The invention provides a method of inhibiting interferon regulatory factor 5 (IRF5) in a patient in need thereof, comprising administering to the patient one or more of any of the polypeptides disclosed herein in an amount effective to inhibit IRF5 in a patient.

The invention provides a method of inhibiting interferon regulatory factor 5 (IRF5) nuclear translocation in a patient in need thereof, comprising administering to the patient one or more of any of the polypeptides disclosed herein in an amount effective to inhibit IRF5 nuclear translocation in a patient. The invention provides polypeptides that bind directly to IRF5 to inhibit IRF5 nuclear translocation.

In the methods disclosed herein, the patient can have an autoimmune disease.

The invention provides a method for treating an autoimmune disease in a patient in need of such treatment, comprising administering to the patient one or more of any of the polypeptides disclosed herein in an amount effective to inhibit IRF5 in a patient.

The autoimmune disease can be, for example, any one or more of systemic lupus erythematosus (SLE), systemic sclerosis (scleroderma), polymyositis/dermatomyositis, Crohn's disease, rheumatoid arthritis, periodontitis, SLE-associated atherosclerosis, Sjögren's syndrome, autoimmune encephalomyelitis, sarcoidosis, Behçet's disease, myasthenia gravis, lupus nephritis, inflammatory bowel disease, ankylosing spondylitis, primary biliary cirrhosis, colitis, juvenile idiopathic arthritis, pulmonary fibrosis, antiphospholipid syndrome and psoriasis.

In the methods disclosed herein, the patient can have classical Hodgkin lymphoma, atherosclerosis, cardiovascular disease, neuropathic pain, leukemia (e.g., T cell large granular lymphocyte leukemia) or lymphoma.

The invention provides a method for treating a patient having classical Hodgkin lymphoma, atherosclerosis, cardiovascular disease, neuropathic pain, leukemia (e.g., T cell large granular lymphocyte leukemia) or lymphoma, comprising administering to the patient one or more of any of the polypeptides disclosed herein in an amount effective to inhibit IRF5 in a patient.

Any of the treatment methods disclosed herein can further comprise administering a second therapeutic agent to the patient.

The invention provides one or more of any of the polypeptides disclosed herein for use in medical treatment or diagnosis or for preparation of a medicament for inhibiting interferon regulatory factor 5 (IRF5).

The invention provides a research agent for studying interferon regulatory factor 5 (IRF5) comprising one or more of any of the polypeptides disclosed herein.

The invention provides a kit comprising one or more of any of the polypeptides disclosed herein, at least one other therapeutic agent, and instructions for administering the polypeptide and the other therapeutic agent(s) to a patient to treat an autoimmune disease, classical Hodgkin lymphoma, atherosclerosis, cardiovascular disease, neuropathic pain, leukemia (e.g., T cell large granular lymphocyte leukemia) or lymphoma.

The patient can be any mammal. Preferably, the patient is a human.

"And/or" as used herein, for example, with option A and/or option B, encompasses the embodiments of (i) option A, (ii) option B, and (iii) option A plus option B.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Materials and Methods

Study Design and Methods. The main objectives of this program were to design a small library of cell permeable peptide mimetics that directly bind to and inhibit IRF5 activation as therapeutic candidates against SLE and other disease conditions in which IRF5 activation contributes to pathogenesis.

Synthesis of IRF5 Peptide inhibitors. Peptides were synthesized by LifeTein, LLC and purity confirmed by HPLC and mass spectrometry (Table 1). A peptide consisting of the cell permeable sequence alone, designated Cell Penetrating Peptide 1 (CPP1) (SEQ ID NO:4), was used as a negative control. Peptides 1-5 (N5-1 (SEQ ID NO:20), N5-2 (SEQ ID NO:17), N5-3 (SEQ ID NO:18), N5-4 (SEQ ID NO:19), N5-5 (SEQ ID NO:21)) correspond to N-terminal sequences of IRF5; C5-2 (SEQ ID NO:22) corresponds to a C-terminal sequence of IRF5. Individual peptides conjugated to FITC were also synthesized for uptake experiments.

Surface Plasmon Resonance (SPR) Analysis. The Biacore T200 (GE Healthcare, UK) was used for real-time binding interaction studies. Full-length recombinant IRF5 protein (ab173024, Abcam) was immobilized onto a CMS series chip (GE Healthcare) by diluting to a concentration of 20 μg/mL in 10 mM acetate buffer (pH=5.0). A 1:1 mixture of N-hyrdoxysuccinimide and N-ethyl-N-(dimethyaminopropyl)carbodiimide was used to activate 2 flow-cells of the CMS chip. One flow-cell was used as a reference and thus immediately blocked upon activation by 1 M ethanolamine (pH=8.5). The sample flow-cell was injected with the diluted IRF5 at a flow rate of 10 μL/min by manual injection. The IRF5 injection was stopped when the SPR reached ~490 RU. For binding of peptides to IRF5, the analytes (peptides) were diluted to 1 μM in 1×PBS+0.05% Tween20 buffer, filtered (0.22 μm) and injected over the IRF5 immobilized chip at a flow rate of 30 μL/min for 60 s at 25° C. with a dissociation time set for 1 min. Binding experiments were conducted in 1×PBS+0.05% Tween20 as the running buffer; at least 3 independent experiments were performed.

Imaging Flow Cytometry. Imaging flow was performed as previously described on the Amnis Imagestream (19). Briefly, PBMCs from healthy donors were isolated and treated with inhibitor for 1 h, subsequently stimulated with R848 (500 ng/mL) or 2% SLE serum for 2 h, followed by staining for CD19 and CD14. PBMC were then fixed overnight in 1% paraformaldehyde and then permeabilized (19). Permeabilized cells were blocked in 5% BSA solution and stained for intracellular IRF5 (Abcam Catalog #: ab193245) or phospho(pSer462)IRF5 and FITC-conjugated secondary antibody (Abcam Catalog #: ab6896). Prior to acquisition, DRAQ5 dye was added at a 1:50 dilution. PBMC from SLE patients were only surface-stained and permeabilzed for intracellular IRF5 and DRAQ5 staining. Murine PBMC were stained similarly for intracellular IRF5 (Abcam Catolog #: 181553) (58) and APC-conjugated secondary antibody (BioLegend). Images were acquired on the ImageStream using the 40× objective. Nuclear translocation was quantified in the Amnis IDEAS software suite. Briefly, cells were first filtered through the brightfield area vs. brightfield aspect ratio gate to exclude non-viable and doublet events. Following which a similar gate of the DRAQ5 nuclear channel was used. This added an extra measure of stringency for cell viability. Images were gated on either CD14$^+$IRF5$^+$, CD19$^+$IRF5$^+$, or CD123$^+$BDCA2$^+$IRF5$^+$ events, followed by gating on images with a Gradient RMS of greater than 20 on the DRAQ5 channel. This was done to select images with a high level of clarity. Finally, IRF5 nuclear translocation was determined through use of the similarity score feature contrasting IRF5 staining with DRAQ5 staining. A similarity score≥2 was considered a translocation event.

Results

Design of peptide mimetics that specifically bind to IRF5. Given that IRF5 is hyper-activated in immune cells from SLE patients and NZB/W F1 lupus mice, we designed a series of inhibitors that would potentially bind to and target IRF5 activation. We used data from IRF crystal structures and IRF5 DN mutants (2,26,28,37) to generate a series of peptide mimetics that correspond to the N-terminus of IRF5 with the intent to stabilize or maintain the inactive IRF5 monomer, thus inhibiting IRF5 nuclear translocation. Since a crystal structure containing the IRF5 N-terminus has yet to be resolved (28), and the DNA binding domain (DBD) of IRFs is highly homologous, we used coordinates from the resolved IRF3 DBD to build an N-terminal homology model of IRF5 (42). This model was used to predict amino acid sequences with different characteristics to promote interaction with the IRF5 C-terminus. Sequence predictions were based on solvent accessible surface, charge, and hydrophobicity (Table 1). In order for the peptides to transduce the cell membrane, IRF5 sequences were combined with a protein transduction domain, in this case CPP1 (SEQ ID NO:4). CPP1 (SEQ ID NO:4) has been previously shown to facilitate cell permeability of small peptides (43).

Peptides (1 μM) were tested for their ability to directly interact with human full-length recombinant IRF5 variant 5 (isoform V5) by surface plasmon resonance (SPR) analysis. DWEYS (SEQ ID NO:23) peptide served as a non-targeted control and CPP1 (SEQ ID NO:4) as a control for the cell permeable sequence. As expected, DWEYS (SEQ ID NO:23) showed no affinity for IRF5 and CPP1 (SEQ ID NO:4) had minimal binding affinity. N5-1 (SEQ ID NO:20) and N5-2 (SEQ ID NO:17) showed the strongest binding affinity for IRF5, with N5-3 (SEQ ID NO:18) binding to a slightly lesser extent; N5-5 (SEQ ID NO:21) showed no affinity for IRF5 (binding affinity for IRF5: N5-1 (SEQ ID NO:20)≥N5-2 (SEQ ID NO:17)>N5-3 (SEQ ID NO:18) >N5-4 (SEQ ID NO:19)>CPP1 (SEQ ID NO:4)>N5-5 (SEQ ID NO:21)). A shared similarity between N5-1 (SEQ ID NO:20) and N5-2 (SEQ ID NO:17) is their relatively stronger positive charge, as compared to the others (Table 1).

Human IRF5 contains two nuclear localization signals (NLS), one in the N-terminus and one in the C-terminus (27). N5-1 (SEQ ID NO:20) corresponds to the N-terminal NLS (PRRVRLK) (SEQ ID NO:24). To test whether any NLS is capable of binding to IRF5, we generated C5-2 (SEQ ID NO:22) that corresponds to the C-terminal NLS of IRF5 (PREKKLI) (SEQ ID NO:25) and examined binding by SPR. C5-2 (SEQ ID NO:22) and CPP1 (SEQ ID NO:4) bound with similar low affinities. We have thus identified first generation peptide mimetics N5-1 (SEQ ID NO:20), N5-2 (SEQ ID NO:17) and N5-3 (SEQ ID NO:18) that directly bind to the full-length inactive IRF5 monomer. The observed difference in function between N5-1 (SEQ ID NO:20) and C5-2 (SEQ ID NO:22) supports that the NLS is not the driver of inhibitor activity and instead, peptide mimetics showing the strongest binding affinity for IRF5, N5-1 (SEQ ID NO:20) and N5-2 (SEQ ID NO:17) are those positively charged and relatively surface accessible.

Peptide mimetics inhibit TLR7-induced IRF5 nuclear translocation. We next sought to determine whether in vitro binding data would translate into IRF5 cellular inhibition. IRF5 is a key downstream mediator of TLR7-induced cytokine expression and TLR7 signaling has been implicated in SLE pathogenesis (2,44-47). We examined the ability of IRF5 peptide mimetics to inhibit IRF5 nuclear translocation following stimulation of PBMC with R848. We focused on peptides that showed binding to IRF5 by SPR analysis and included CPP1 (SEQ ID NO:4) and C5-2 (SEQ ID NO:22) as negative controls. For the initial screening, isolated PBMC from healthy donors were pre-incubated in the presence of mock (PBS), or 10 μM CPP1 (SEQ ID NO:4), N5-1 (SEQ ID NO:20), N5-2 (SEQ ID NO:17), N5-3 (SEQ ID NO:18) or C5-2 (SEQ ID NO:22) inhibitor for 1 h followed by stimulation with 500 ng/mL of R848 for 2 h. Cells were surface-stained with anti-CD14 (monocytes or Mo) and anti-CD19 (B cells) antibodies, then permeabilized and stained for intracellular IRF5 and DRAQ5. As expected, R848 induced significant IRF5 nuclear translocation in mock-incubated Mo (2) and B cells. While pre-incubation with CPP1 (SEQ ID NO:4) had no significant effect on R848-induced IRF5 nuclear translocation in either cell type, N5-1 (SEQ ID NO:20), N5-2 (SEQ ID NO:17) and N5-3 (SEQ ID NO:18) provided a significant reduction in R848-induced nuclear translocation in Mo.

Discussion

Signaling pathways have emerged as key targets for the development of small molecule inhibitors, with the primary targets being protein kinases and phosphatases (48,49). A caveat to this type of therapeutic targeting, however, is that it requires a priori knowledge of the signaling molecules leading to activation. Second, kinase inhibitors are generally not specific to one kinase, one signaling pathway, nor one downstream target protein. In the case of IRF5, it is well-documented that IRF5 becomes activated in a cell type- and stimuli-dependent manner (1,26,30-32,50-52). Regulation of IFN and inflammatory cytokine production by IRF5 requires nuclear translocation whereby it transcriptionally modulates target gene expression. Previous work suggested a requirement for ubiquitination and/or acetylation before phosphorylation and homo/heterodimerization, which may or may not ultimately lead to nuclear translocation to occur (32,53,54). Further, IRF5 phosphorylation occurs at multiple sites, which is dependent on the pathway of activation (27-32). Thus, in order to bypass the ambiguity of post-translational modifications and dimerization, we developed peptide mimetics that directly bind to and inhibit IRF5 activation (nuclear translocation) independent of the initiating pathway. We report selective IRF5 inhibitors that directly bind to endogenous, intracellular IRF5 to inhibit nuclear translocation (55,56). This identifies these fusion peptides as inhibitors of IRF5 with therapeutic potential in inflammatory and autoimmune diseases where IRF5 activation contributes to pathogenesis, such as lupus.

TABLE 1

IRF5 peptide inhibitor sequences, charge distribution and hydrophobicity.

| Peptide Inhibitor | Sequence | Charge |
|---|---|---|
| Cell Penetrating Peptide 1 (CPP1) SEQ ID NO: 4 | DRQIKIWFQNRRMK WKK | positive |
| N5-1 (SEQ ID NO: 20) | DRQIKIWFQNRRMK WKKPRRVRLK | positive |
| N5-2 SEQ ID NO: 17 | DRQIKIWFQNRRMK WKKRHATRHG | positive |
| N5-3 SEQ ID NO: 18 | DRQIKIWFQNRRMK WKKKSRDFRL | +/- |
| N5-4 SEQ ID NO: 19 | DRQIKIWFQNRRMK WKKGPRDMPP | hydrophobic |
| N5-5 (SEQ ID NO: 21) | DRQIKIWFQNRRMK WKKEGVDEAD | negative |
| C5-2 (SEQ ID NO: 22) | DRQIKIWFQNRRMK WKKPREKKLI | +/- |
| FITC-CPP1 (SEQ ID NO: 4) | FITC-DRQIKIWFQNRR MKWKK | SAA |
| FITC-N5-1 (SEQ ID NO: 20) | FITC-DRQIKIWFQNRR MKWKKPRRVRLK | SAA |
| FITC-C5-2 (SEQ ID NO: 22) | FITC-DRQIKIWFQNRR MKWKKPREKKLI | SAA |
| Non-specific control (SEQ ID NO: 23) | DWEYS | negative |

SAA-same as above.

REFERENCES

1. B. J. Barnes, P. A. Moore, P. M. Pitha, Virus-specific activation of a novel interferon regulatory factor, IRF-5, results in the induction of distinct interferon alpha genes. *J. Biol. Chem.* 276, 23382-23390 (2001).
2. A. Schoenemeyer, B. J. Barnes, M. E. Mancl, E. Latz, N. Goutagny, P. M. Pitha, K. A. Fitzgerald, D. T. Golenbock, The interferon regulatory factor, IRF5, is a central mediator of toll-like receptor 7 signaling. *J. Biol. Chem.* 280, 17005-17012 (2005).
3. A. Takaoka, H. Yanai, S. Kondo, G. Duncan, H. Negishi, T. Mizutani, S. Kano, K. Honda, Y. Ohba, T. W. Mak, T. Taniguchi, Integral role of IRF-5 in the gene induction programme activated by Toll-like receptors. *Nature* 434, 243-249 (2005).
4. D. Savitsky, T. Tamura, H. Yanai, T. Taniguchi, Regulation of immunity and oncogenesis by the IRF transcription factor family. *Cancer Immunol. Immunother.* 59, 489-510 (2010).
5. H. L. Eames, A. L. Corbin, I. A. Udalova, Interferon regulatory factor 5 in human autoimmunity and murine models of autoimmune disease. *Transl. Res.* 167, 167-182 (2016).
6. R. R. Graham, S. V. Kozyrev, E. C. Baechler, M. V. Reddy, R. M. Plenge, J. W. Bauer, W. A. Ortmann, T. Koeuth, M. F. González Escribano; Argentine and Spanish Collaborative Groups, B. Pons-Estel, M. Petri, M. Daly, P. K. Gregersen, J. Martín, D. Altshuler, T. W. Behrens, M. E. Alarcón-Riquelme, A common haplotype of interferon regulatory factor 5 (IRF5) regulates splicing and expression and is associated with increased risk of systemic lupus erythematosus. *Nature Genet.* 38, 550-555 (2006).
7. G. M. Hirschfield, X. Liu, Y. Han, I. P. Gorlov, Y. Lu, C. Xu, Y. Lu, W. Chen, B. D. Juran, C. Coltescu, A. L. Mason, P. Milkiewicz, R. P. Myers, J. A. Odin, V. A. Luketic, D. Speiciene, C. Vincent, C. Levy, P. K. Gregersen, J. Zhang, E. J. Heathcote, K. N. Lazaridis, C. I. Amos, K. A. Siminovitch, Variants at IRF5-TNPO3, 17q12-21 and MMEL1 are associated with primary biliary cirrhosis. *Nature Genet.* 42, 655-657 (2010).
8. K. Dawidowicz, Y. Allanore, M. Guedj, C. Pierlot, S. Bombardieri, A. Balsa, R. Westhovens, P. Barrera, H. Alves, V. H. Teixeira, E. Petit-Teixeira, L. van de Putte, P. van Riel, B. Prum, T. Bardin, O. Meyer, F. Cornélis, P. Dieudé; ECRAF, The interferon regulatory factor 5 gene confers susceptibility to rheumatoid arthritis and influences its erosive phenotype. *Ann. Rheum. Dis.* 70, 117-121 (2011).
9. G. Gathungu, C. K. Zhang, W. Zhang, J. H. Cho, A two-marker haplotype in the IRF5 gene is associated with inflammatory bowel disease in a North American cohort. *Genes Immun,* 13, 351-355 (2012).
10. R. Saigusa, Y. Asano, T. Taniguchi, T. Yamashita, Y. Ichimura, T. Takahashi, T. Toyama, A. Yoshizaki, K. Sugawara, D. Tsuruta, T. Taniguchi, S. Sato, Multifaceted contribution of the TLR4-activated IRF5 transcription factor in systemic sclerosis. *Proc. Natl. Acad. Sci. USA* 112, 15136-15141 (2015).
11. B. Matta, S. Song, D. Li, B. J. Barnes, Interferon regulatory factor signaling in autoimmune disease. *Cytokine* 98, 15-26 (2017).
12. J. Banchereau J, V. Pascual, Type I interferon in systemic lupus erythematosus and other autoimmune diseases. *Immunity* 25, 383-392 (2006).
13. E. Tackey, P. E. Lipsky, G. G. Illei, Rationale for interleukin-6 blockade in systemic lupus erythematosus. *Lupus* 13, 339-343 (2004).
14. R. Banchereau, S. Hong, B. Cantarel, N. Baldwin, J. Baisch, M. Edens, A. M. Cepika, P. Acs, J. Turner, E. Anguiano, P. Vinod, S. Khan, G. Obermoser, D. Blankenship, E. Wakeland, L. Nassi, A. Gotte, M. Punaro, Y. J. Liu, J. Banchereau, J. Rossello-Urgell, T. Wright, V.

Pascual, Personalized Immunomonitoring Uncovers Molecular Networks that Stratify Lupus Patients. *Cell* 165, 551-565 (2016).
15. Q. Z. Li, J. Zhou, Y. Lian, B. Zhang, V. K. Branch, F. Carr-Johnson, D. R. Karp, C. Mohan, E. K. Wakeland, N. J. Olsen, Interferon signature gene expression is correlated with autoantibody profiles in patients with incomplete lupus syndromes. *Clinical Exp. Immunol.* 159, 281-291 (2010).
16. L. Ronnblom, M. L. Eloranta, G. V. Alm, The type I interferon system in systemic lupus erythematosus. *Arthritis Rheum.* 54, 408-420 (2006).
17. B. J. Ripley, B. Goncalves, D. A. Isenberg, D. S. Latchman, A. Rahman, Raised levels of interleukin 6 in systemic lupus erythematosus correlate with anaemia. *Ann. Rheum. Dis.* 64, 849-853 (2005).
18. D. Feng, R. C. Stone, M. L. Eloranta, N. Sangster-Guity, G. Nordmark, S. Sigurdsson, C. Wang, G. Alm, A. C. Syvanen, L. Ronnblom, B. J. Barnes, Genetic variants and disease-associated factors contribute to enhanced interferon regulatory factor 5 expression in blood cells of patients with systemic lupus erythematosus. *Arthritis Rheum.* 62, 562-573 (2010).
19. R. C. Stone, D. Feng, J. Deng, S. Singh, L. Yang, P. Fitzgerald-Bocarsly, M. L. Eloranta, L. Rönnblom, B. J. Barnes, Interferon regulatory factor 5 activation in monocytes of systemic lupus erythematosus patients is triggered by circulating autoantigens independent of type I interferons. *Arthritis Rheum.* 64, 788-798 (2012).
20. D. Feng, L. Yang, X. Bi, R. C. Stone, P. Patel, B. J. Barnes, Irf5-deficient mice are protected from pristane-induced lupus via increased Th2 cytokines and altered IgG class switching. *European J. Immunol.* 42, 1477-1487 (2012).
21. K. Yasuda, A. A. Watkins, G. S. Kochar, G. E. Wilson, B. Laskow, C. Richez, R. G. Bonegio, I. R. Rifkin, Interferon regulatory factor-5 deficiency ameliorates disease severity in the MRL/lpr mouse model of lupus in the absence of a mutation in DOCK2. *PLoS One* 9, e103478 (2012).
22. A. A. Watkins, K. Yasuda, G. E. Wilson, T. Aprahamian, Y. Xie, E. Maganto-Garcia, P. Shukla, L. Oberlander, B. Laskow, H. Menn-Josephy, Y. Wu, P. Duffau, S. K. Fried, A. H. Lichtman, R. G. Bonegio, I. R. Rifkin, IRF5 deficiency ameliorates lupus but promotes atherosclerosis and metabolic dysfunction in a mouse model of lupus-associated atherosclerosis. *J. Immunol.* 194, 1467-1479 (2015).
23. M. Manni, S. Gupta, E. Ricker, Y. Chinenov, S. H. Park, M. Shi, T. Pannellini, R. Jessberger, L. B. Ivashkiv, A. B. Pernis, Regulation of age-associated B cells by IRF5 in systemic autoimmunity. *Nat. Immunol.* 19, 407-419 (2018).
24. M. Hedl, C. Abraham, IRF5 risk polymorphisms contribute to interindividual variance in pattern recognition receptor-mediated cytokine secretion in human monocyte-derived cells. *J. Immunol.* 188, 5348-5356 (2012).
25. D. A. Savitsky, H. Yanai, T. Tamura, T. Taniguchi, K. Honda, Contribution of IRF5 in B cells to the development of murine SLE-like disease through its transcriptional control of the IgG2a locus. *Proc. Natl. Acad. Sci. USA* 107, 10154-10159 (2010).
26. M. E. Mancl, G. Hu, N. Sangster-Guity, S. L. Olshalsky, K. Hoops, P. Fitzgerald-Bocarsly, P. M. Pitha, K. Pinder, B. J. Barnes, Two discrete promoters regulate the alternatively spliced human interferon regulatory factor-5 isoforms. Multiple isoforms with distinct cell type-specific expression, localization, regulation, and function. *J. Biol. Chem.* 280, 21078-21090 (2005).
27. B. J. Barnes, M. J. Kellum, A. E. Field, P. M. Pitha, Multiple regulatory domains of IRF-5 control activation, cellular localization, and induction of chemokines that mediate recruitment of T lymphocytes. *Mol. Cell. Biol.* 22, 5721-5740 (2002).
28. W. Chen, S. S. Lam, H. Srinath, Z. Jiang, J. J. Correia, C. A. Schiffer, K. A. Fitzgerald, K. Lin, W. E. Royer Jr, Insights into interferon regulatory factor activation from the crystal structure of dimeric IRF5. *Nature Struct. Mol. Biol.* 15, 1213-1220 (2008).
29. R. Lin, L. Yang, M. Arguello, C. Panefuerte, J. Hiscott, A CRM1-dependent nuclear export pathway is involved in the regulation of IRF-5 subcellular localization. *J. Biol. Chem.* 280, 3088-3095 (2005).
30. J. Ren, X. Chen, Z. Chen, IKKbeta is an IRF5 kinase that instigates inflammation. *Proc. Natl. Acad. Sci. USA* 111, 17438-17443 (2014).
31. M. Lopez-Pelaez, D. J. Lamont, M. Peggie, N. Shapiro, N. S. Gray, P. Cohen. Protein kinase IKKbeta-catalyzed phosphorylation of IRF5 at Ser462 induces its dimerization and nuclear translocation in myeloid cells. *Proc. Natl. Acad. Sci. USA* 111, 17432-17437 (2014).
32. H. C. Chang Foreman, S. Van Scoy, T. F. Cheng, N. C. Reich, Activation of interferon regulatory factor 5 by site specific phosphorylation. *PLoS One* 7, e33098 (2012).
33. F. Alzaid, F. Lagadec, M. Albuquerque, R. Ballaire, L. Orliaguet, I. Hainault, C. Blugeon, S. Lemoine, A. Lehuen, D. G. Saliba, I. A. Udalova, V. Paradis, F. Foufelle, N. Venteclef, IRF5 governs liver macrophage activation that promotes hepatic fibrosis in mice and humans. *JCI Insight* 1, e88689 (2016).
34. K. Sun, J. Qu, J. Chen, S. Dang, S. He, J. Zhang, R. Xie, Y. Wang, J. Zhang, IRF5 regulates lung macrophages M2 polarization during severe acute pancreatitis in vitro. *World J Gastroenterol.* 22, 9368-9377 (2016).
35. A. J. Byrne, M. Weiss, S. A. Mathie, S. A. Walker, H. L. Eames, D. Saliba, C. M. Lloyd, I. A. Udalova, A critical role for IRF5 in regulating allergic airway inflammation. *Mucosal. Immunol.* 10, 716-726 (2016).
36. E. Lazzari, C. A. Jefferies, IRF5-mediated signaling and implications for SLE. *Clin. Immunol.* 153, 343-352 (2014).
37. H. J. Martin, J. M. Lee, D. Walls, S. D. Hayward, Manipulation of the toll-like receptor 7 signaling pathways by epstein-barr virus. *J. Virol.* 81, 9748-9758 (2007).
38. L. Yang, T. Zhao, X. Shi, P. Nakhaei, Y. Wang, Q. Sun, J. Hiscott, R. Lin, Functional analysis of a dominant negative mutation of interferon regulatory factor 5. *PLoS One* 4, e5500 (2009).
39. Z. Ren, Y. Wang, D. Tao, D. Liebenson, T. Liggett, R. Goswami, R. Clarke, D. Stefoski, R. Balabanov, Overexpression of the dominant-negative form of interferon regulatory factor 1 in oligodendrocytes protects against experimental autoimmune encephalomyelitis. *J. Neurosci.* 31, 8329-8341 (2011).
40. T. Y. Kim, K. H. Lee, S. Chang, C. Chung, H. W. Lee, J. Yim, T. K. Kim, Oncogenic potential of a dominant negative mutant of interferon regulatory factor 3. *J. Biol. Chem.* 278, 15272-15278 (2003).
41. S. Ning, L. E. Huye, J. S. Pagano, Regulation of the transcriptional activity of the IRF7 promoter by a pathway independent of interferon signaling. *J. Biol. Chem.* 280, 12262-12270 (2005).

42. K. Takahasi, N. N. Suzuki, M. Horiuchi, M. Mori, W. Suhara, Y. Okabe, Y. Fukuhara, H. Terasawa, S. Akira, T. Fujita, F. Inagaki, X-ray crystal structure of IRF-3 and its functional implications. *Nat. Struct. Biol.* 10, 922-927 (2003).
43. Y-Z. Lin, S. Y. Yao, R. A. Veach, R. R. Torgerson, J. Hawiger, Inhibition of nuclear translocation of transcription factor NF-κB by a synthetic peptide containing a cell membrane-permeable motif and nuclear localization sequence. *J. Biol. Chem.* 270, 14255-14258 (1995).
44. A. Komatsuda, H. Wakui, K. Iwamoto, K. Sawada, Up-regulated expression of Toll-like receptors mRNAs in peripheral blood mononuclear cells from patients with systemic lupus erythematosus. *Clin. Exp. Immunol.* 152, 482-487 (2008).
45. B. D. Lyn-Cook, C. Xie, J. Oates, E. Treadwell, B. Word, G. Hammons, K. Wiley, Increased expression of Toll-like receptors (TLRs) 7 and 9 and other cytokines in systemic lupus erythematosus (SLE) patients: ethnic differences and potential new targets for therapeutic drugs. *Mol. Immunol.* 61, 38-43 (2014).
46. S. Subramanian, K. Tus, Q. Z. Li, A. Wang, X. H. Tian, J. Zhou, C. Liang, G. Bartov, L. D. McDaniel, X. J. Zhou, R. A. Schultz, E. K. Wakeland, A Tlr7 translocation accelerates systemic autoimmunity in murine lupus. *Proc. Natl. Acad. Sci. USA* 103, 9970-9975 (2006).
47. P. Pisitkun, J. A. Deane, M. J. Difilippantonio, T. Tarasenko, A. B. Satterthwaite, S. Bolland, Autoreactive B cell responses to RNA-related antigens due to TLR7 gene duplication. *Science* 312, 1669-1672 (2006).
48. P. Cohen, Protein kinases—the major drug targets of the twenty-first century? *Nat. Rev. Drug Discov.* 1, 309-315 (2002).
49. P. A. Ott, S. Adams, Small-molecule protein kinase inhibitors and their effects on the immune system: implications for cancer treatment. *Immunotherapy* 3, 213-227 (2011).
50. L. Cushing, A. Winkler, S. A. Jelinsky, K. Lee, W. Korver, R. Hawtin, V. R. Rao, M. Fleming, L. L. Lin, IRAK4 kinase activity controls Toll-like receptor-induced inflammation through the transcription factor IRF5 in primary human monocytes. *J. Biol. Chem.* 292, 18689-18698 (2017).
51. G. Hu, M. E. Mancl, B. J. Barnes, Signaling through IFN regulatory factor-5 sensitizes p53-deficient tumors to DNA damage-induced apoptosis and cell death. *Canc Res.* 65, 7403-7412 (2005).
52. G. Hu, B. J. Barnes, IRF-5 is a mediator of the death receptor-induced apoptotic signaling pathway. *J. Biol. Chem.* 284, 2767-2777 (2009).
53. M. Y. Balkhi, K. A. Fitzgerald, P. M. Pitha, Functional regulation of MyD88-activated interferon regulatory factor 5 by K63-linked polyubiquitination. *Mol. Cell. Biol.* 28, 7296-7308 (2008).
54. D. Feng, N. Sangster-Guity, R. C. Stone, J. Korczeniewska, M. E. Mancl, P. Fitzgerald-Bocarsly, B. J. Barnes, Differential requirement of histone acetylase and deacetylase activities for IRF5-mediated proinflammatory cytokine expression. *J. Immunol.* 185, 6003-6012 (2010).
55. H. Xu, J. G. Krolikowski, D. W. Jones, Z. D. Ge, P. S. Pagel, K. A. Pritchard Jr, D. Weihrauch, 4F decreases IRF5 expression and activation in hearts of tight skin mice. *PLoS One* 7, e52046 (2012).
56. D. Weihrauch, J. G. Krolikowski, D. W. Jones, T. Zaman, O. Bamkile, J. Struve, S. Pillai, P. S. Pagal, N. L. Lohr, K. A. Pritchard Jr, An IRF5 decoy peptide reduces myocardial inflammation and fibrosis and improves endothelial cell function in tight-skin mice. *PLoS One* 11, e0151999 (2016).
57. M. A. Doucey, L. Goffin, D. Naeher, O. Michielin, P. Baumgartner, P. Guillaume, E. Palmer, I. F. Luescher, CD36 establishes a functional link between the T cell receptor and CD8. *J. Biol. Chem.* 278, 3257-3264 (2003).
58. D. Li, S. De, D. Li, S. Song, B. Matta, B. J. Barnes, Specific detection of interferon regulatory factor 5 (IRF5): A case of antibody equality. *Sci. Rep.* 6, 31002 (2016).
59. United States Patent Application Publication No. 2020/0071370 A1, published Mar. 5, 2020, BJ. Barnes, Cell Penetrating Peptides that Inhibit IRF5 Nuclear Localization.

What is claimed is:

1. A polypeptide consisting of a cell penetrating amino acid sequence and an interferon regulatory factor 5 (IRF5) targeting amino acid sequence, wherein the IRF5 targeting amino acid sequence consists of one or more of RHATRHG (SEQ ID NO:1), KSRDFRL (SEQ ID NO:2) and GPRDMPP (SEQ ID NO:3).

2. The polypeptide of claim 1, wherein the cell penetrating amino acid sequence comprises a sequence at least 90% identical to DRQIKIWFQNRRMKWKK (SEQ ID NO: 4), AAVALLPAVLLALLAP (SEQ ID NO:5), GRKKRRQRRRPPQ (SEQ ID NO:6), CSIPPEVKFNKPFVYLI (SEQ ID NO:7), KKWKMRRNQFWVKVQRG (SEQ ID NO:8), KLLKLLLKLWLKLLKLLL (SEQ ID NO:9), INLKALAALAKKIL (SEQ ID NO:10), RQIKIWFQNRRMKWKKGG (SEQ ID NO:11), GWTLNSAGYLLGKINLKALAALAKKIL (SEQ ID NO:12), YLKFIPLKRAIWLIK ID NO: 13), (SEQ MANLGYWLLALFVTMWTDVGLCKKRPKP (SEQ ID NO:14), RQIKIWFQNRRMKWKK (SEQ ID NO:15) or LCLRPVG (SEQ ID NO:16).

3. The polypeptide of claim 1, wherein the cell penetrating amino acid sequence comprises DRQIKIWFQNRRMKWKK (SEQ ID NO:4), AAVALLPAVLLALLAP (SEQ ID NO:5), GRKKRRQRRRPPQ (SEQ ID NO:6), CSIPPEVKFNKPFVYLI (SEQ ID NO:7), KKWKMRRNQFWVKVQRG (SEQ ID NO:8), KLLKLLLKLWLKLLKLLL (SEQ ID NO:9), INLKALAALAKKIL (SEQ ID NO:10), RQIKIWFQNRRMKWKKGG (SEQ ID NO:11), GWTLNSAGYLLGKINLKALAALAKKIL (SEQ ID NO:12), (SEQ YLKFIPLKRAIWLIK ID NO: 13), MANLGYWLLA- LFVTMWTDVGLCKKRPKP (SEQ ID NO:14), RQIKIWFQNRRMKWKK (SEQ ID NO:15) or LCLRPVG (SEQ ID NO:16).

4. A polypeptide comprising a cell penetrating amino acid sequence and an interferon regulatory factor 5 (IRF5) targeting amino acid sequence, wherein the polypeptide comprises an amino acid sequence at least 90% identical to DRQIKIWFQNRRMKWKKRHATRHG (SEQ ID NO:17), DRQIKIWFQNRRMKWKKKSRDFRL (SEQ ID NO:18) or DRQIKIWFQNRRMKWKKGPRDMPP (SEQ ID NO:19).

5. A polypeptide comprising a cell penetrating amino acid sequence and an interferon regulatory factor 5 (IRF5) targeting amino acid sequence, wherein the polypeptide comprises amino acid sequence DRQIKIWFQNRRMKWKKRHATRHG (SEQ ID NO: 17), DRQIKIWFQNRRMKWKKKSRDFRL (SEQ ID NO:18) or DRQIKIWFQNRRMKWKKGPRDMPP (SEQ ID NO:19).

6. The polypeptide of claim 4, wherein the polypeptide consists of an amino acid sequence at least 90% identical to DRQIKIWFQNRRMKWKKRHATRHG (SEQ ID NO: 17), DRQIKIWFQNRRMKWKKKSRDFRL (SEQ ID NO:18) or DRQIKIWFQNRRMKWKKGPRDMPP (SEQ ID NO:19).

7. The polypeptide of claim 5, wherein the polypeptide consists of amino acid sequence DRQIKIWFQNRRMKWKKRHATRHG (SEQ ID NO:17), DRQIKIWFQNRRMKWKKKSRDFRL (SEQ ID NO: 18) or DRQIKIWFQNRRMKWKKGPRDMPP (SEQ ID NO:19).

8. A nucleic acid sequence encoding the polypeptide of claim 1.

9. A pharmaceutical composition comprising the polypeptide of claim 1 and a pharmaceutically acceptable carrier.

10. A kit comprising the polypeptide of claim 1, at least one other therapeutic agent, and instructions for administering the polypeptide and the other therapeutic agent(s) to a patient to treat an autoimmune disease, classical Hodgkin lymphoma, atherosclerosis, cardiovascular disease, neuropathic pain, leukemia or lymphoma.

11. The polypeptide of claim 1, wherein the cell penetrating amino acid sequence is selected from the group consisting of DRQIKIWFQNRRMKWKK (SEQ ID NO:4), AAVALLPAVLLALLAP (SEQ ID NO:5), GRKKRRQRRRPPQ (SEQ ID NO:6), CSIPPEVKFNKPFVYLI (SEQ ID NO:7), KKWKMRRNQFWVKVQRG (SEQ ID NO:8), KLLKLLLKLWLKLLKLLL (SEQ ID NO:9), INLKALAALAKKIL (SEQ ID NO:10), RQIKIWFQNRRMKWKKGG (SEQ ID NO:11), GWTLNSAGYLLGKINLKALAALAKKIL (SEQ ID NO:12), YLKFIPLKRAIWLIK (SEQ ID NO:13), MANLGYWLLALFVTMWTDVGLCKKRPKP (SEQ ID NO:14), RQIKIWFQNRRMKWKK (SEQ ID NO:15) and LCLRPVG (SEQ ID NO:16).

* * * * *